US00PP32303P3

(12) United States Plant Patent
Stephens

(10) Patent No.: US PP32,303 P3
(45) Date of Patent: Oct. 13, 2020

(54) RASPBERRY PLANT NAMED 'NN10062'

(50) Latin Name: ***Rubus idaeus* L.**
Varietal Denomination: NN10062

(71) Applicant: Pacific Berries, LLC, Lynden, WA (US)

(72) Inventor: Joseph Stephens, Upper Moutere (NZ)

(73) Assignee: Pacific Berries, LLC, Lynden, WA (US)

( * ) Notice: Subject to any disclaimer, the term of this patent is extended or adjusted under 35 U.S.C. 154(b) by 0 days.

(21) Appl. No.: 16/501,398

(22) Filed: Apr. 5, 2019

(65) Prior Publication Data

US 2019/0335635 P1 Oct. 31, 2019

Related U.S. Application Data

(60) Provisional application No. 62/686,526, filed on Jun. 18, 2018.

(30) Foreign Application Priority Data

Apr. 30, 2018 (CA) ..... PBR 18-9436

(51) Int. Cl.
*A01H 5/08* (2018.01)
*A01H 6/74* (2018.01)

(52) U.S. Cl.
USPC ..... Plt./204
CPC ..... *A01H 6/7499* (2018.05)

(58) Field of Classification Search
USPC ..... Plt./204
CPC ..... A01H 6/7499; A01H 5/08
See application file for complete search history.

*Primary Examiner* — Keith O. Robinson
(74) *Attorney, Agent, or Firm* — Leydig, Voit & Mayer, Ltd.

(57) ABSTRACT

A new and distinct floricane-fruiting red raspberry, *Rubus idaeus* L., variety is described. The new variety is distinguished from others by, medium-large, firm, fruit that have dark red skin color and ripens late season. Fruit of the new variety appears very suitable for machine harvesting and the process fruit market.

4 Drawing Sheets

CROSS-REFERENCE TO RELATED APPLICATIONS

This application is a U.S. Nonprovisional Plant Application filed under 35 U.S.C. § 111(*a*) which claims the benefit of U.S. Provisional Application No. 62/686,526, filed Jun. 18, 2018, and Canadian Application No. PBR 18-9436, filed Apr. 30, 2018. This application is hereby incorporated by reference in its entirety.

Genus and species plant claimed: *Rubus idaeus* L.
Variety denomination: 'NN10062'.

BACKGROUND OF THE INVENTION

The new variety of red raspberry, *Rubus idaeus* L., was created in the course of a planned breeding program carried out at Lynden, Wash., USA. It was selected from a population of seedlings derived from a controlled cross carried out in 2007 between 'Wakefield' (seed parent) (U.S. Plant Pat. No. 21,185) and ZN06004 (pollen parent) (not patented). The original plant of the new variety was selected in 2010 for suitability for machine harvesting and for process markets. In 2012 'NN10062' was asexually propagated by tissue culture. The resulting plants were planted at Lynden, Wash., USA and were subsequently found to be true to type demonstrating that the characteristics of the new variety, 'NN10062', are stable and transmitted without change through succeeding generations.

SUMMARY OF THE INVENTION

'NN10062' is characterised by having canes with no spines and medium-large, firm, dark red fruit suitable for machine harvesting and for processing.

'NN10062' is distinguished from a number of varieties by the following characteristics:

When compared to 'Meeker' (not patented), 'NN10062' fruit is darker in red skin color, and harvests later than 'Meeker'. In addition, the canes of 'NN10062' have no spines while 'Meeker' has spines.

When compared to the maternal parent 'Wakefield', 'NN10062' fruit ripens slightly earlier than 'Wakefield' and the canes have no spines while 'Wakefield' cane has spines.

When compared to the paternal parent, ZN06004, 'NN10062' fruit is firmer and ripens later. In addition, 'NN10062' has no spines on the canes while ZN06004 has spines.

BRIEF DESCRIPTION OF THE DRAWINGS

The accompanying photographs show typical specimens of the plant, fruit, and cane of the new variety depicted in colors as nearly true as is reasonably possible to make the same color in illustrations of this character.

DETAILED DESCRIPTION

Figure 1:
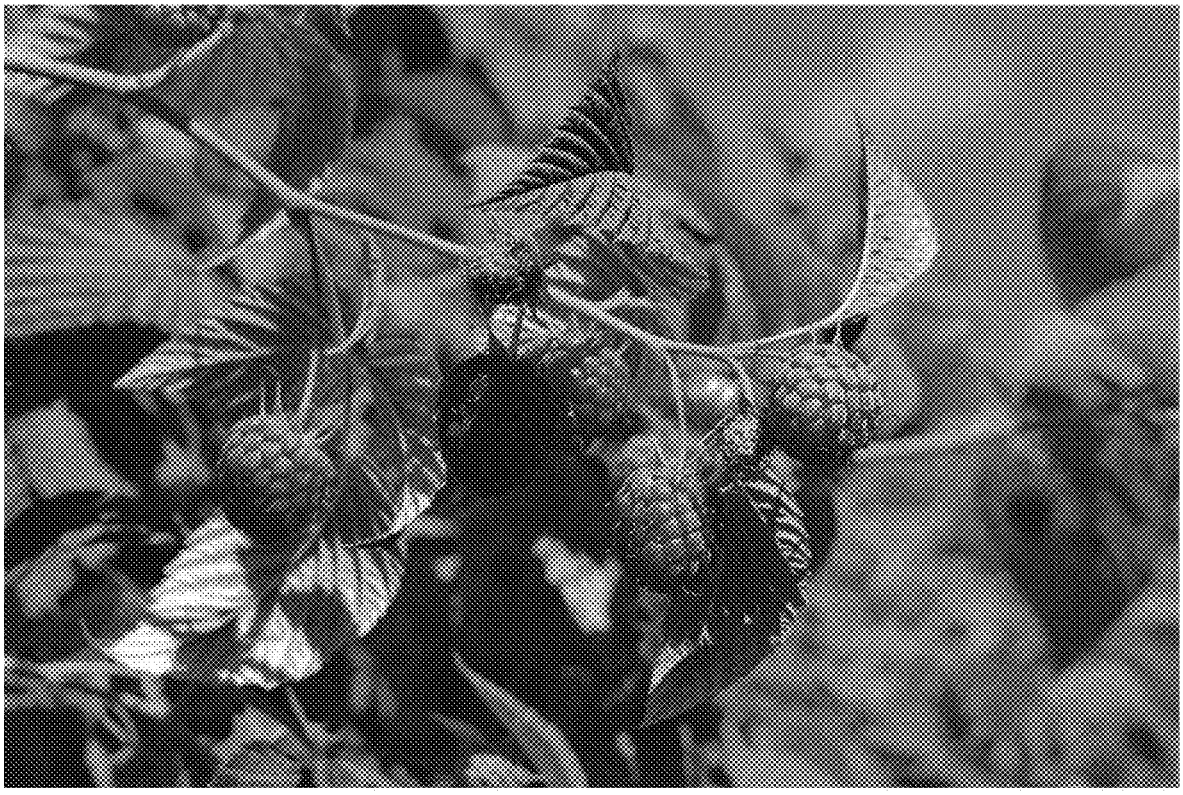
FIG. 1: 'NN10062' fruit on plant.
Figure 2:
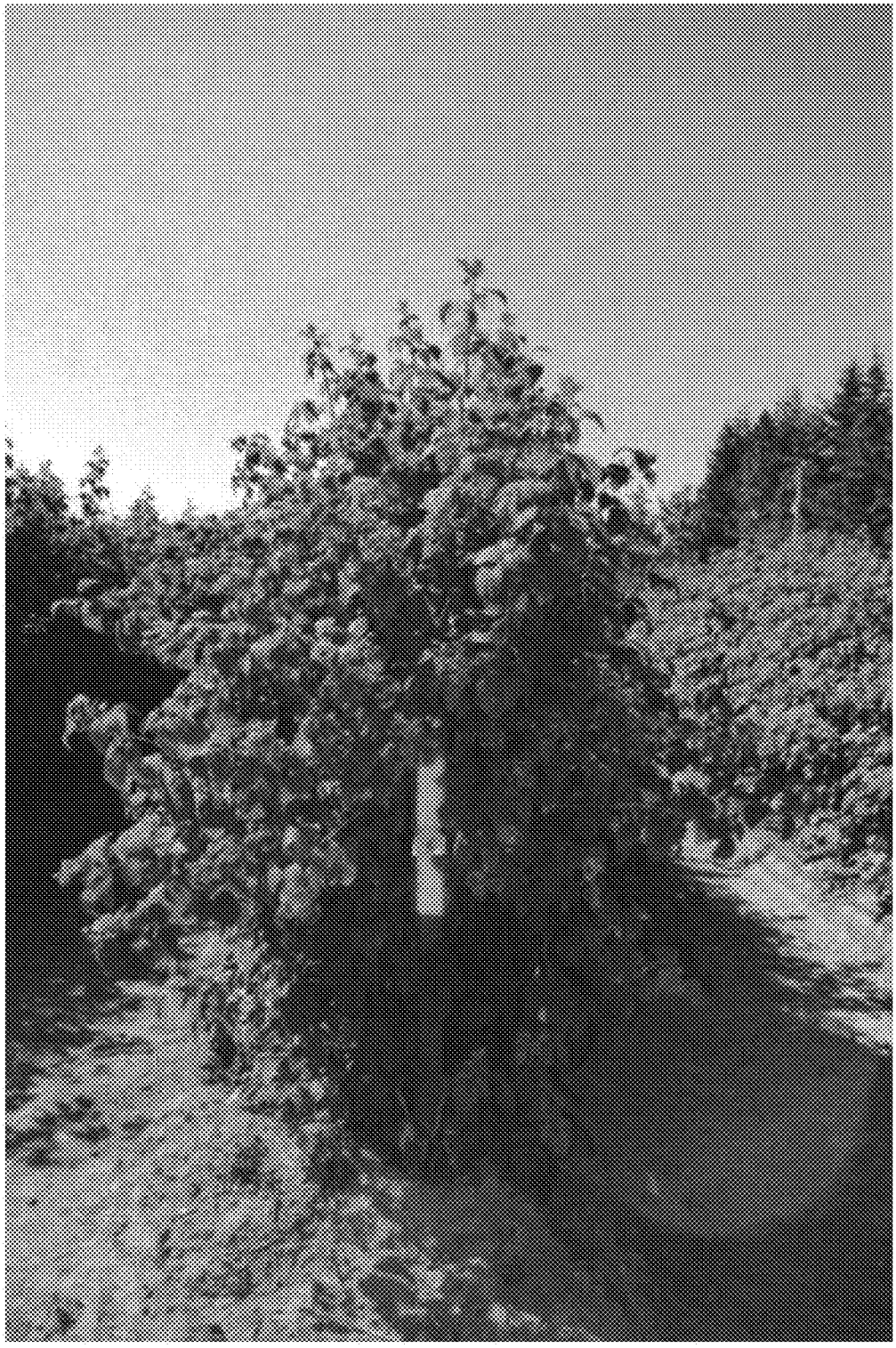
FIG. 2: 'NN10062' one-year old plant.
Figure 3:
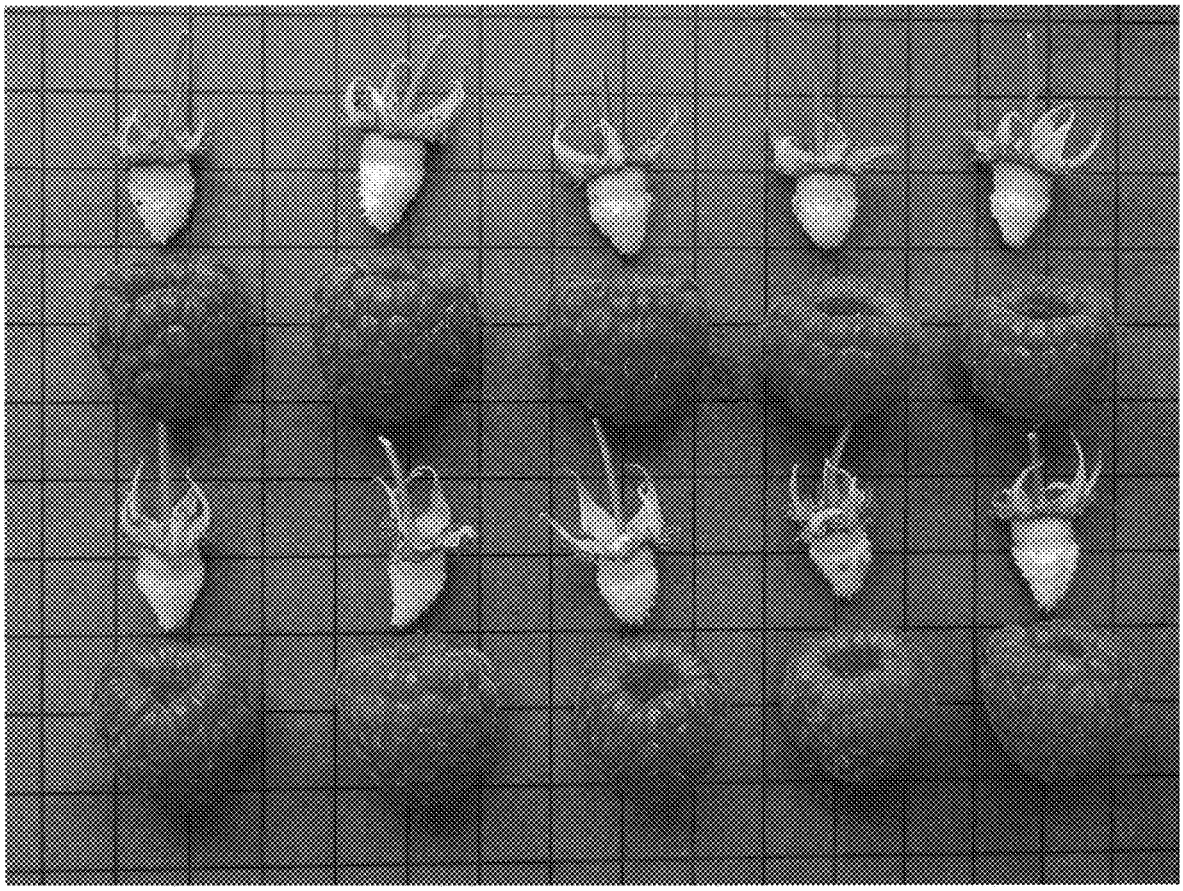
FIG. 3: 'NN10062' fruit and receptacle
Figure 4:
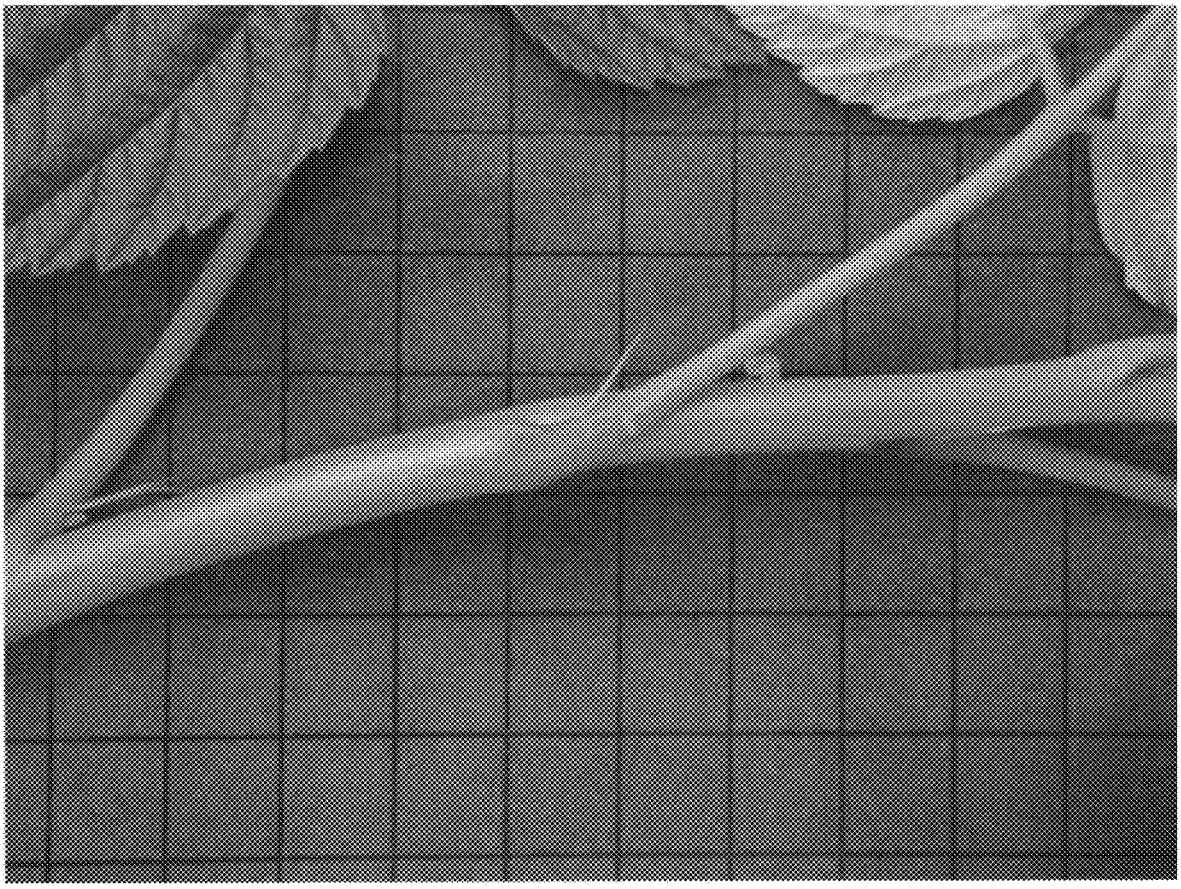
FIG. 4: 'NN10062' cane tip with no spines

Horticultural terminology is used in accordance with UPOV guidelines for raspberry. All dimensions are in millimeters, weights in grams (unless otherwise stated). Where a color reference is given these refer to The R.H.S. Color Chart, The Royal Horticultural Society, London, 5$^{th}$ Edition, 2007. The specimens described were grown in Lynden, Wash., USA. The plants were one and two years old and measurements taken in 2016 and 2017.

Environmental data for the Lynden, Wash., USA growing area demonstrates conditions in spring and early summer (equating to the harvest period for the variety) as follows:

Spring (April/May); mean daily temperature in the range 10-11° C. (mean daily minimum 5.5° C., mean daily maximum 15.5° C.).

Early summer (June/July); mean daily temperature 16° C. (mean daily minimum 10° C., mean daily maximum 21.5° C.).

In winter temperatures below 0° C. are common, the daily mean for December/January is 2.5° C. with the lowest temperature unlikely to be colder than −13° C. Average annual rainfall is approximately 1500 mm.

Plant and foliage: Plants exhibited a strong, open, upright growth habit. Time of cane emergence was late. Average plant height was approximately 2.1 m and average cane length approximately 250 cm. There was an average of 38 nodes per cane with an internode average length of 11 cm. The average diameter of the canes at 1-1.5 m height was 10 mm. Spines were absent. Very fine cane pubescence (controlled by what is known as gene H) was present. The color of the mature cane on the sunny side was near greyed-purple 183A and on the shady side near yellow-green 145A. Young shoots were erect in attitude and were near yellow-green 146D in color. There was no anthocyanin coloration of the growing tip. Three leaflets were present. The terminal leaflet shape of the apex was pointed and the shape of the base was cordate. The shape of the leaf upper side in cross section was flat to convex. The upper side of the leaf was glabrous with moderate puckering. Average total leaf length was 15 cm, average total leaf width was 17 cm, average terminal leaflet length was 10 cm and average terminal leaflet width was 6 cm. Leaf color on the upper side was near green 137B and near yellow-green 146A and the lower side was near greyed-green 194A. The leaf margin was biserrate and leaf rugosity was medium. There was pronounced leaf venation and the vein coloration was near yellow-green 145B. Average leaf petiole length was 52 mm and average diameter was 2 mm. Petiole color was near yellow-green 145A with anthocyanin coloration on the upper side near greyed-red 180A. Hairs were present on the petioles.

Inflorescence: Flowers were arranged in a paniculate inflorescence, singly and in pairs. The pedicel on the sunny side was near greyed-purple 184A and on the shady side the color was near yellow-green 144B. Small hairs, averaging less than 0.3 mm in length were present on the pedicel. Average peduncle length was 19 mm and average diameter 1 mm. The color of the peduncle yellow-green 144A with moderate anthocyanin coloration. Flowers had five sepals and were near yellow-green 145B. Average sepal length was 9mm. Average diameter of the terminal flower was 24 mm. Five petals were present and average petal length was 7 mm and average width 2.7 mm. The petal shape was obovate, the shape of the tip obtuse and the shape of the base truncate. The petals had moderate venation and the margins were entire with some undulation near apex. The primary color of the petals was white 155C. Flowers contained an average of 105 stamens and average length of the stamen filament was 4 mm. The color of the stamens and filaments were near white NN155D. The anthers were approximately 0.5 mm in length and near grey-brown 199D in color. Approximately 70 stigma were present per flower and the color of the stigma was near green-white 157A. Flower fragrance was absent.

Fruit: Fruit was produced only on previous year's cane in Summer. Fruit was conical in shape and average berry weight was 4 g, average length 19 mm and average width 21 mm. Fruit had a receptacle which had an average length of 12 mm and average width of 8 mm. Fruit skin color and flesh color was near greyed-purple 187B. Skin had low gloss and hairs were present. The width of an average single drupelet was 4 mm. Fruit was firm. The fruiting laterals were horizontal to slightly drooping in shape and the length was medium, with an average of 840 mm. Soluble solids concentration averaged 10.2° Brix. The fruit had high levels of anthocyanins, ellagitannins and Vitamin C. The average total anthocyanin levels over three seasons was 138.8 mg/100 g, and average total ellagitannins 117.4 mg/100 g, and average Vitamin C 27.8 mg/100 g.

Harvest: 'NN10062' fruit harvested late season later than 'Meeker'. It was very suitable for harvest by machine due to the ease with which fruit dislodged from the receptacle. Fruit was firm and well suited to individually quick frozen (IQF) operations. The dark red color of the fruit means it was also suitable for other types of processing markets. In machine harvested trials in the Pacific North west, USA, the average fruit yield over several seasons was 5.0 t/acre.

Events: Vegetative bud burst occurred late season; beginning of flowering occurred late season; and beginning of fruit ripening occurred late season.

Pest and disease resistance: 'NN10062' has tested negative to numerous RBDV tests using enzyme-linked immunosorbent assay (ELISA) and no RBDV symptoms have been seen in the field on plants resulting in the conclusion that 'NN10062' is likely to be resistant to RBDV found in the USA. In field trials in the Pacific North West, USA, 'NN10062' appears to have some tolerance to root rot caused by *Phytophthora rubi.*

Geographical adaption: Observations indicate that the variety is well-suited to production in regions that offer a medium-high amount of winter chill, for example, 'NN10062' performs well in USDA Plant Hardiness zones 8-10 (published as the 2003 US National Arboretum "Web Version" of the USDA Plant Hardiness Zone Map USDA Miscellaneous Publication No. 1475, Issued January 1990).

The invention claimed is:

1. A new and distinct raspberry plant substantially as illustrated and described.

* * * * *